United States Patent
Wertz et al.

[11] Patent Number: 5,120,126
[45] Date of Patent: Jun. 9, 1992

[54] SYSTEM FOR NON-CONTACT COLORED LABEL IDENTIFICATION AND INSPECTION AND METHOD THEREFOR

[75] Inventors: Ronald D. Wertz, Boulder; Jeffrey P. Davies, Louisville; Robert H. Cormack, Boulder, all of Colo.

[73] Assignee: Ball Corporation, Muncie, Ind.

[21] Appl. No.: 715,802

[22] Filed: Jun. 14, 1991

[51] Int. Cl.⁵ .................. G01N 21/27; G01N 21/90; G06K 9/68
[52] U.S. Cl. .................................. 356/71; 356/328; 356/237; 250/226
[58] Field of Search ............. 356/71, 328, 237, 239, 356/402; 250/226

[56] References Cited

U.S. PATENT DOCUMENTS

| | | | |
|---|---|---|---|
| 3,676,645 | 6/1972 | Fickenscher et al. | |
| 3,745,527 | 7/1973 | Yoshimura et al. | |
| 4,270,863 | 6/1981 | Trogdon | 356/71 |
| 4,589,141 | 5/1986 | Christian et al. | 382/14 |
| 4,790,022 | 12/1988 | Dennis | 382/8 |
| 4,797,937 | 1/1989 | Tajima | 382/31 |
| 4,809,342 | 2/1989 | Kappner | 382/11 |
| 4,859,863 | 8/1989 | Schrader et al. | 250/556 |
| 4,881,268 | 11/1989 | Uchida | 382/7 |

OTHER PUBLICATIONS

Cutler-Hammer Product Information (EATON). Multiple LED, Color Sensing, By Gregory L. Nadolski.

Primary Examiner—Vincent P. McGraw
Attorney, Agent, or Firm—Dorr, Carson, Sloan & Peterson

[57] ABSTRACT

An optical inspection system which inspects for the presence of defects in colored labels placed, for example, on the side walls of cylindrical beverage cans. The optical inspection system utilizes a conveyor for conveying the beverage cans in a production line where such beverage cans typically are randomly oriented. The optical inspection system positions an optical head near the beverage cans as they move in the production line without physically interferring or interacting with the movement. The optical head senses a preselected number of different colors which appear in a predetermined field of view of each moving can. The cans being randomly oriented have different portions of the label visible in the predetermined field of view which is fixed in position. The optical head produces analog electrical signals corresponding to the intensity of each sensed color. A computer is utilized to process these analog electrical signals from the optical head. The computer first generates a number of two color signatures based upon the selected number of colors. After sufficient cans have passed the optical head wherein all two color signatures are fully developed, the computer senses the colors from each successive subsequent can and compares it to the generated color signature. if the sensed color pattern falls outside the generated color signatures, then the can fails and an air signal is generated.

22 Claims, 7 Drawing Sheets

SYSTEM FOR NON-CONTACT COLORED LABEL IDENTIFICATION AND INSPECTION AND METHOD THEREFOR

BACKGROUND OF THE INVENTION

1. Field of the Invention

The present invention relates to the non-contact identification and inspection of colored labels and, in particular, the identification and inspection of colored labels on containers such as beverage cans traveling at high speeds through a production line.

2. Statement of the Problem

A need exists for a low cost, high speed system for identifying and inspecting labels such as those found on beverage cans in an assembly line environment. Furthermore, the system should adjust to the label configuration so that it can automatically learn the overall color signatures of a label and once the learning process is accomplished, the system should automatically adapt to inspect all subsequent labels. The system should be able to function independently of the orientation of the label and of production line speed, yet capable of operating at high speeds such as 2000 cans per minute. The system must not physically contact with the label or interfere with the flow of the containers on the production line. Finally, the system should be capable of inspecting the label for fine defects such as grease spots and scratches on the order of one square centimeter, small changes in color wavelength and intensity, and changes in color balance due to ink smears.

3. Results of a Patentability Search

With the above statement of the problem and the teachings of the present invention in mind, a patentability search was conducted. The results were:

| INVENTOR | PATENT No. | ISSUE DATE |
|---|---|---|
| Fickenscher et. al. | 3,676,645 | 7-11-72 |
| Yoshimura et al. | 3,745,527 | 7-10-73 |
| Trogdon | 4,270,863 | 6-2-81 |
| Christian et. al. | 4,589,141 | 5-13-86 |
| Dennis | 4,790,022 | 12-6-88 |
| Tajima | 4,797,937 | 1-10-89 |
| Kappner | 4,809,342 | 2-28-89 |
| Schrader et al. | 4,859,863 | 8-22-89 |
| Uchida et al. | 4,881,268 | 11-14-89 |

The 1989 patent to Uchida pertains to a system using optical fiber bundles disposed so as to identify a particular type of bank note by detecting colors from reflected or transmitted light. The Uchida approach utilizes three color detecting sensors to receive reflective light from a selected linear path on the bank notes being inspected. Hence, Uchida is limited in that it does not perform a complete label inspection, but rather only narrow linear portions of the bank note. Hence, defects occurring in other portions of the bank note not in a linear path of one of the detectors would remain undetected. Furthermore, the Uchida sensor utilizes optical fiber bundles which must be located in close proximity to the surface of the bank note. As the bank note moves, a time varying signal is generated. The signal variation repeats for each bank note and, therefore, is cyclical. The time varying signals received by the sensors are processed by hardware into two color components (e.g., blue/red) and the ratio of these components (i.e., red/blue) is obtained. The resulting ratio signal is then compared with a predetermined reference pattern signal which is stored in memory. The bank notes must be precisely oriented in delivery due to the narrow color region being examined. The Uchida system is incapable of self learning and must be provided with the referenced pattern.

The 1988 patent to Dennis sets forth the use of a color camera which produces gamma-corrected RGB output that is fed to three picture stores for green, red, and blue components. This output is delivered through analog to digital converters into a microprocessor. The signal output, like Uchida, is time varying but it is not cyclical since the vegetables are randomly provided. The Dennis approach is suitable for analyzing color differences in vegetables moving along the conveyor line (such as green spots in potatoes). As such, the vegetables can be oriented in any direction and they can be of differing sizes and shapes. Dennis looks for a particular color pattern of perhaps a size and shade that renders the vegetable defective. The system must be first calibrated by utilizing an actual potato containing a defect having an undesirable shade of green and the system is then capable of detecting the transition between the green defect area and the color of the surrounding potato. Dennis detects only a transition defect in a color specific background by using two or three dimensional color patterns stored in a three dimensional memory (which is implemented in three separate two-dimensional look-up tables). This approach is unsuitable for detecting small defects in labels.

Yoshimura provides for precisely oriented postage stamps being delivered through a scanner. Again, this approach is not suitable for randomly oriented containers such as beverage cans in an assembly line. However, Yoshimura only utilizes the three reflected colors: red, green, and blue to address a lookup table to assign a region a color (i.e. red, green, blue or white) based upon the combination of the three inputs. These signals are time varying and are precisely based upon the known geometrics of the stamp's design.

The 1989 patent to Schrader is a label inspection apparatus which senses overall reflectivity values of labels moving in a conveyor line at conveyor speeds of 100 to 600 containers per minute with containers spaced at three inch clearances. Labels up to six inches can be read. The invention uses a linear array of photo detectors arranged at $\frac{1}{2}$ inch centers on a vertical line. A microprocessor is used to calculate the percentage reflectivity values and pass or fail limits are established for the containers. The invention also includes a learn cycle wherein a sufficiently large statistical sample of containers are read to determine the overall reflectivity values which will represent the entire population of containers to be inspected.

The 1989 patent to Kappner sets forth a process for identifying and recognizing objects such as permanent coding. This invention is able to identify a precise coordinate position for the coded symbols on the object.

The 1989 patent to Tajima pertains to an apparatus for identifying postage stamps. This invention scans postage stamps and detects the various colors contained thereon and which are located at predetermined regions on the stamp. The received color signals are used to produce a feature vector which represents the color distribution over the scanned area. Sensor arrays are used to produce red, green, and blue color analog electrical signals which are digitized based upon color moments within a defined area. The sensor arrays are designed to provide a scanning line and the stamps must be precisely delivered to insure the scanning line integrity.

The 1986 patent to Christian pertains to a computer vision apparatus for automatically inspecting printed labels. This system first goes through a teach phase in which the label is memorized by the system. Secondly, it goes through an inspection phase in which unknown labels are then inspected.

The 1981 patent to Trogdon (U.S. Pat. No. 4,270,863) and assigned to Owen-Illinois Inc. sets forth an apparatus for illuminating the surface of the label and then generating an intensity level for a number of points on the surface of the label which are sensed by a photo sensitive diode array. The intensity levels are then compared with a stored maximum value and if different from that value, a good or bad signal is generated. This invention utilizes a learning process by inspecting a number of labels, storing that information, and then using the stored information to do the inspection. This invention utilizes a camera having a 128 by 128 array. An A/D converter receives the camera analog video signals to generate a digitized signal.

The 1972 patent to Fickenscher sets forth a label reader using a rotating faceted mirror.

It is believed that Uchida et al., Dennis, and Yoshimura, et al. are the most pertinent to the teachings of the present invention. However, Uchida, et al. requires precision in the delivery of each stamp to the three narrow line scanners; Dennis, Uchida, et al. and Yoshimura, et al. all require that the system be initialized with reference values. None of these approaches are designed to sample the entire surface of uniformly shaped objects by first learning the color signatures for the object entire label automatically and then finely inspecting for color defects.

The aforementioned Uchida, Yoshimura and Dennis patents each store time varying signals and then process those signals to generate color differences vs. position. The generated color signals are compared to the stored color values. A need still exists for a system to obtain single color samples for randomly-oriented object being tested and to accumulate such samples to obtain an overall spatial color signature of the label on the object which is insensitive to scan rate and which utilizes simple hardware and memory.

4. Solution to the Problem

The present invention provides a solution to the above problem by providing a low cost, high speed system for identifying and inspecting labels such as those found on beverage cans in a high speed production line environment. The present invention is capable of performing process defect inspection independent of scan rate, yet operating at high rates of conveyor speeds such as 800 feet per minute (i.e., providing a can delivery rate of up to 2000 cans per minute). The system of the present invention utilizes one optical head, in one embodiment, to first sample the passing labels in order to learn and to construct the color signature for the entire labels. When satisfied that learning is completed, the system then automatically configures to optically inspect each successive can.

The present invention can have its sensitivity selectively adjusted with maximum sensitivity occurring in twenty-eight different color dimensions coupled with minimum data dilation. Furthermore, the orientation of the label can be random as it passes the optical head and the system of the present invention is still capable of learning the color signatures and performing inspection of the label. The optical inspection system of the present invention does not physically contact with the label or interfere in any fashion with the flow of containers on the production line except to provide a reject signal for those can(s) that need to be rejected.

The system of the present invention is capable of inspecting for defects such as grease spots and scratches on the order of one square centimeter, small changes in color wavelength and intensity, and changes in color balance due to ink smears.

One overriding difference exists between the Uchida, Yoshimura and Dennis approaches and the approach of the present invention. This difference is in the method that the signature is collected. All three of the prior art machines gather a set of time varying signals produced by moving the object in front of the sensor or by scanning the sensor field of view across the object. What is collected in each case is a signature that contains information regarding the spatial color characteristics of the label on the object. These signals are then processed to generate spatial difference signals.

The present invention collects single samples of the color signature every time a label passes in front of the sensor. If a number of labels pass the sensor displaying different data (i.e., either different parts of a label or the same label in different orientations or a combination of both), that information can be collected to eventually generate a complete color signature set for the entire label. The information collected on each single pass is different due to the label's spatial orientation, but that spatial orientation is not incorporated into the learned data. Thus, the signature learned by the present invention can be either a function of the varying characteristics of the object along its length or of the varying orientation of the object with respect to the sensor. Since a spatial difference signal is not generated by the present invention, the scan rate and delay characteristics do not affect the performance. The present invention operates at any line speed from full stop to the maximum rate.

The hardware and software requirements of having to store the data from an entire object scan are eliminated with the present invention since it only collects single samples from each data channel every pass. In the case of the Dennis invention, a significant hardware savings is realized in eliminating the color TV camera, video frame buffers, and associated control circuitry. In the Dennis and Yoshimura inventions, a significant amount of hardware is dedicated to the delay and add functions not required by the present invention.

A second fundamental difference between the present invention and the other prior art approaches set forth above involves the manner in which the present invention produces the color separated signals. The other systems utilize filters over the sensors, or a color TV camera. The present invention passes the reflected light from the can through a transmissive diffraction grating to separate the component colors. Any diffractive element or a prism could be utilized for this task. This portion of the machine is inexpensive compared to the costs and complexity of all the other systems. Hence, simplicity is achieved through the use of the grating or prism (i.e., there is only one set of optics for the entire system) and no timing or control signals are required except that of the can position sensor.

In comparison to Yoshimura, which is insensitive to irregularities in the object surface and to letter ornamentation and patterns (column 2, line 42), the present invention specifically detects these irregularities. The three-dimensional mapping referred to in Yoshimura is used to characterize a spatial region as red, blue, green, or white based on the RBG inputs from the sensor. This determination is then used to generate appropriate color specific timing signals. The present invention uses the color signals to access a multidimensional memory wherein data is written to perform the learn process or from which data is read to perform the compare process. Thus, the functions of the multidimensional mappings of the present invention are different from Yoshimura. Yoshimura relies heavily on the known and fixed characteristics of the label under test, specifically the relation between the edges and the color borders of the stamps. The present invention assumes no foreknowledge of the label on the object under test and sets no requirements on its characteristics beyond being located within the optical field of view. Yoshimura requires exact placement of the label with respect to the sensor so that a particular region of the label can be compared with the fixed signatures. The present invention is capable of learning label characteristics in any orientation or combination of orientations and aspects of the object. All of the scanned, time varying signals of Yoshimura are further processed by delaying the signal and subtracting it from its original real time signal to create a temporal, and thus a spatial, color difference signal. This signal is then used to generate color-dependent timing signals which create an evaluation metric. Thus, it is the scanned characteristic of Yoshimura which allows it to function. Additionally, the operation of Yoshimura is in part dependent on the scan rate and delay function. The present invention is insensitive to object rate.

In comparison to Uchida which collects a time varying signal from two color sensors and after providing a ratio of the color signals compares them to the stored signature data, the present invention requires no predetermined signatures to make its evaluation. Uchida requires exact placement of the test label with respect to the sensor so that a particular region of the label can be repeatedly compared with the fixed signatures. The present invention is capable of learning label characteristics in any orientation or combination of orientations and aspects of the object carrying the label.

In comparison to Dennis which uses multiple two-dimensional multi-bit tables and logically ANDs their outputs to generate an overall evaluation, the present invention uses only multiple two-dimensional one-bit tables. This results in a savings of computer memory by allowing for the digitization of the color signals into greater numbers of bits than would be practical if multi-bit look-up tables were utilized. Dennis must teach his machine the specific defect to be detected by actually showing the system a sample defect or an image of the sample defect. Furthermore, the sample defect must be seen by the machine against the specific object background on which it can occur (green spot on yellow background, for example). It is this defect signature data that is stored in the look-up tables of the Dennis machine. The present invention is taught what good can labels look like and it detects any deviation from that learned set. Thus any defect may occur on any portion of the label without regard to the surrounding characteristics or defect type. Dennis also relies on scanning the object and, like Yoshimura, creates a spatial color difference signal. These difference signals are then used to access the multiple two-dimensional look-up tables to determine if a defect has been detected. Thus, the actual information that is being stored in the tables is different from that stored in the present invention. Dennis stores spatial color difference signals thereby keying off the color transition at the boundary between a good region and a defective region of the object. The present invention stores the actual color intensities from the portion of the object viewed in memory and keys off any deviation from the learned data.

An important capability of the present invention is its ability to learn object characteristics which vary either because of the object's orientation with respect to the sensor or due to the portion of the object viewed by the sensor. In the can inspection application, the random orientation of the cans is exploited to allow the present invention to learn the characteristics of all aspects of a can label. This is not necessary though. If the cans always passed the sensor showing the same portion of the label, the present invention would simply learn that much of the complete signature and would not perform less satisfactorily since subsequent cans would also present only that same portion of the label for inspection. Defects such as color hue shift, misregistration, etc. could still be detected. Of course, if a physical defect always occurred on the opposite side of the can, it would never be detected, but the same would be true of any of the above discussed approaches.

SUMMARY OF THE INVENTION

The present invention constitutes an optical inspection system which inspects for the presence of defects in colored labels placed, for example, on the side walls of cylindrical beverage cans. The optical inspection system utilizes a conveyor for conveying the beverage cans in a production line typically along a linear path. On this production line, such beverage cans typically are randomly oriented (i.e., the labels occupy different positions with respect to the conveyor), have uneven spacings between the cans, and are usually located unevenly about the center line of the conveyor.

The optical inspection system of the present invention positions an optical head near the beverage cans as they move in the production line without physically interfering or interacting with the movement. The optical head senses a preselected number of different colors (such as red, blue, yellow, and green) which appear in a predetermined field of view of each moving can. As mentioned, the cans are randomly oriented and, therefore, different portions of the label may be visible in the predetermined field of view which is fixed. The optical head produces analog electrical signals corresponding to the intensity of each sensed color.

A computer is utilized to process these analog electrical signals from the optical head. The computer first generates a number (in the preferred invention, 28) of two color signatures based upon the selected number of colors (in the preferred invention four). After sufficient cans have passed the optical head wherein all two color signatures are fully developed, the computer senses the colors from each successive subsequent can and compares it to the generated color signature. If the sensed color pattern falls outside the generated color signatures, then the can fails and an error signal is generated.

DETAILED DESCRIPTION

1. General Overview—

Figure 1:
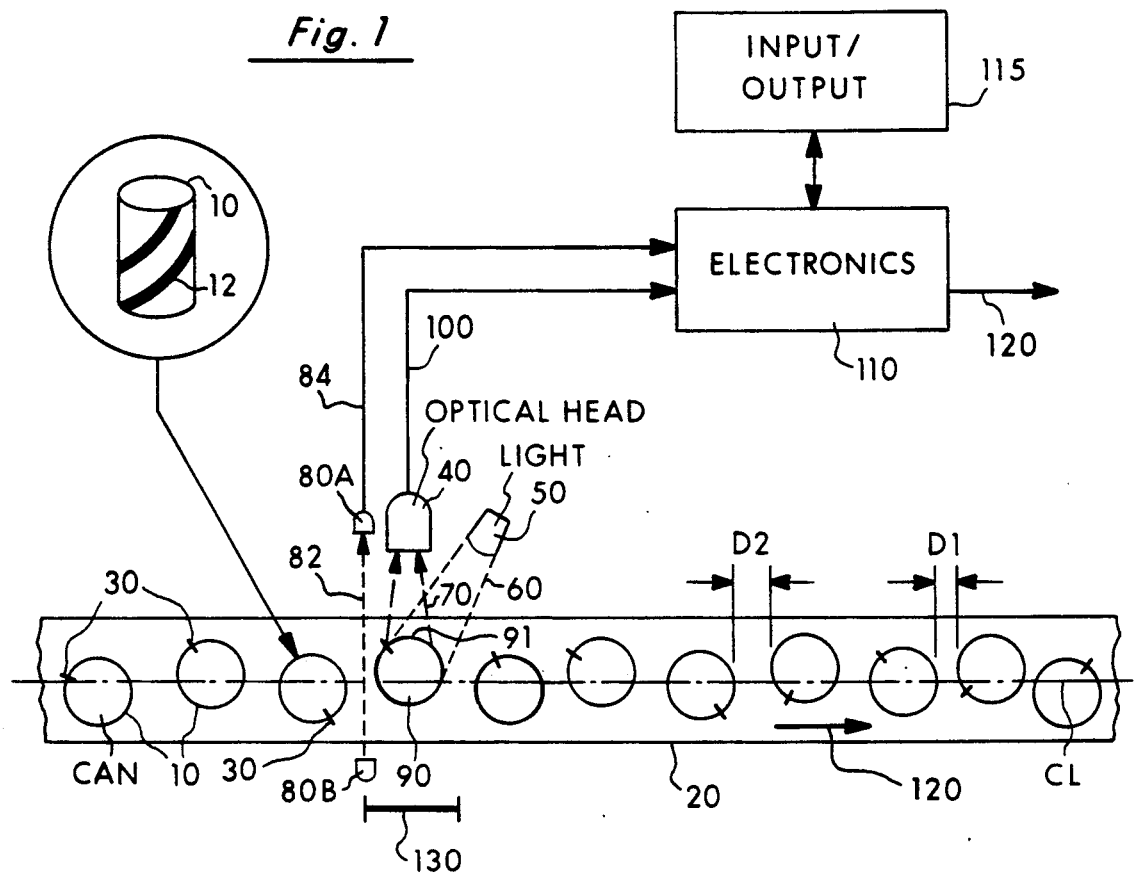
FIG. 1 is an illustration showing the use of a single optical head to learn and inspect beverage cans randomly oriented on a production line.

In FIG. 1, the overall operation of the optical inspection system of the present invention is shown. A plurality of containers 10 such as beverage cans move on a production line 20 in the direction of arrow 120. In typical beverage can production lines, the conveyor line 20 moves at a high rate of speed such as 800 feet per minute providing a can rate of up to 2,000 cans per minute. Each can (herein also termed "object") has a color label 12 which has been placed on the sidewalls of the can usually by a coating, painting, or similar process. The label could also be a paper label which is affixed to the cylindrical sidewalls. The label may or may not go all around the cylindrical sidewalls of the can or extend the full length of the sidewalls. The teachings of the present invention are not limited to beverage cans or other similar cylindrical containers, but has application for detecting defects in flat labels, stamps, bank notes, packaging, and other colored items.

In FIG. 1, each can 10 has a mark 30 which is located on the label at the same point so as to illustrate that the cans 10 can be randomly oriented (and usually are) on the production line 20. The mark 30 is simply used for purposes of illustration in FIG. 1 and is not placed on the actual label. This random orientation of the cans is due to a number of causes such as, for example, vibration on the line 20, physical placement on the line 20 upstream, etc. Additionally, the random orientation of the cans may result in the cans being somewhat unevenly spaced as also illustrated in FIG. 1 by distances D1 and D2. Such cans 30 may be located unevenly about the center line CL. It is to be understood that FIG. 1 emphasizes the irregularities due to random orientation of cans 10 on the conveyor line 20. The present invention is capable of optically inspecting the labels 12 despite such orientation randomness. Clearly, the present invention is capable of optically inspecting the labels on the cans 10 without physically contacting the can or interfering with the production line 20. The present invention also operates on objects of fixed orientation, spacing, and centering.

In FIG. 1, an optical head 40 of the present invention is shown positioned near the cans 10 as the cans are moved along the linear path 120 by the conveyor 20. In the preferred embodiment the optical head 40 is positioned about seven inches from the moving cans. A light source 50 is also provided. The light source 50 provides light 60 which hits the sidewall 90 of a passing can 10 and provides reflective light from a spatial area of the label in a field of view 70 which is directed into the optical head 40. Sensors 80 are provided such as a light source 80b and a photo detector 80a for detecting the presence of a can 10 when a beam of light 82 is broken. Black background 130 being located opposite the sensor head 40 with the can there between presents the sensor head 40 with a uniform, stable reference between cans which is used to remove amplifier drift. Any suitable uniform color could be used.

As shown in FIG. 1, the optical head 40 outputs channels 100 of color signals to electronics 110. Electronics 110 processes these color signals based upon can timing signals delivered over line 84 and when a defect is detected issues an error signal on line 120. The error (or reject) signal accesses conventionally available reject equipment to remove defective cans from the production line 20. Operator input 115 (i.e., keyboard, mouse, touch screen, modem, etc.) and other forms of output (printer, screen, modem, etc.) are conventionally interconnected with electronics 110.

The optical label inspection system of the present invention operates in two fundamental fashions. First, the characteristic color signature of a particular can label is determined or learned by the system by collecting data from a number of cans 10 as they move along the conveyor line 20. For example, the characteristic color signature of a label may be determined with the passage of several hundred cans. As will be explained subsequently, it is not a preselected number of cans that determines the actual number of cans necessary to establish the characteristic color signature, rather it is a sufficient number of cans for the system to conclude that it has a valid characteristic color signature for the entire label. Once the characteristic color signature has been learned, the second mode of operation is entered wherein data from each subsequent can is compared to the color signature to determine whether or not can label 12 conforms to the characteristic color signature. If not, the can is rejected.

Figure 5:
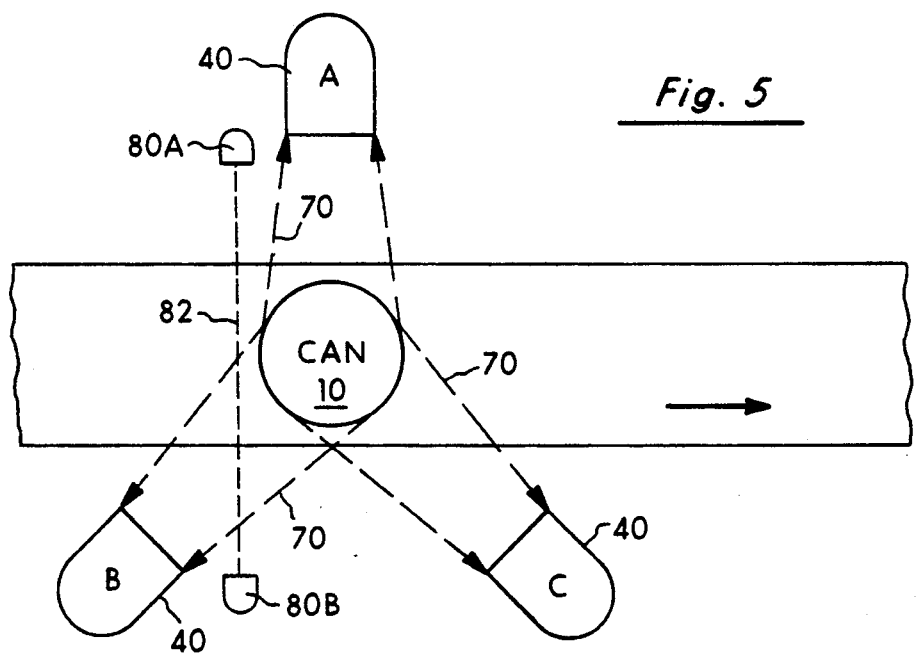
FIG. 5 is an illustration showing the use of three optical heads of the present invention in a first alternate embodiment.

The present invention has the advantage of being able to learn all possible orientations 30 of the label appearing on a can, thus allowing inspection of all subsequent can labels to occur in any orientation. In FIG. 1, the optical head 40 contains a variety of components which receive the reflected light in the field of view 70 carrying an image of a specific spatial area 91 on the sidewall 90 of the label 12 on the container 10. When the can 10 is in the proper position as determined by the can position sensors 80, the set of electrical analog signals appearing on channel 100 which correspond to the colors in the field of view 70 are sampled. In addition, a dark sample is taken between cans so as to offset drift. As shown in FIG. 1, up to 180 degrees of the spatial area 91 of the can label 12 can be inspected with a single optical head 40. It is to be expressly understood that the optical head 40 could be designed to inspect less than 180 degrees of the can label 12. As shown in FIG. 5, multiple optical heads A, B, and C can be utilized to provide a 360 degree spatial area coverage with each optical head being responsible for 120 degrees of the spatial area of the can label. In FIG. 5, the light sources 50 and the black background 130 are not shown in order to fully illustrate the inspection field of each optical head 40.

It is to be expressly understood that the present invention is not limited to the number of optical heads 40, although in the preferred embodiment, only one optical head as shown in FIG. 1 is utilized. It is to be further understood that in FIG. 1, should a defect appear on a portion of an individual label that is not being optically inspected, the defect will be missed. Defects that can be detected include localized paint spots or smears, localized label errors, or nonlocalized errors such as color hue shifts, missing colors, or structural defects of the can itself. However, should the defect be caused by a consistent upstream process problem in the production line, as the cans 10 are delivered in random orientation 30 on the conveyor line 20, then the consistent defect will eventually appear in the field of view of the optical head 40 and be detected. On the other hand, it is to be expressly understood that the arrangement of FIG. 2 provides a full 360 degree coverage of the label on the can 10 such that individual defects appearing on a label could always be detected with respect to a given can.

2. Optical Head 40—

Figure 2:
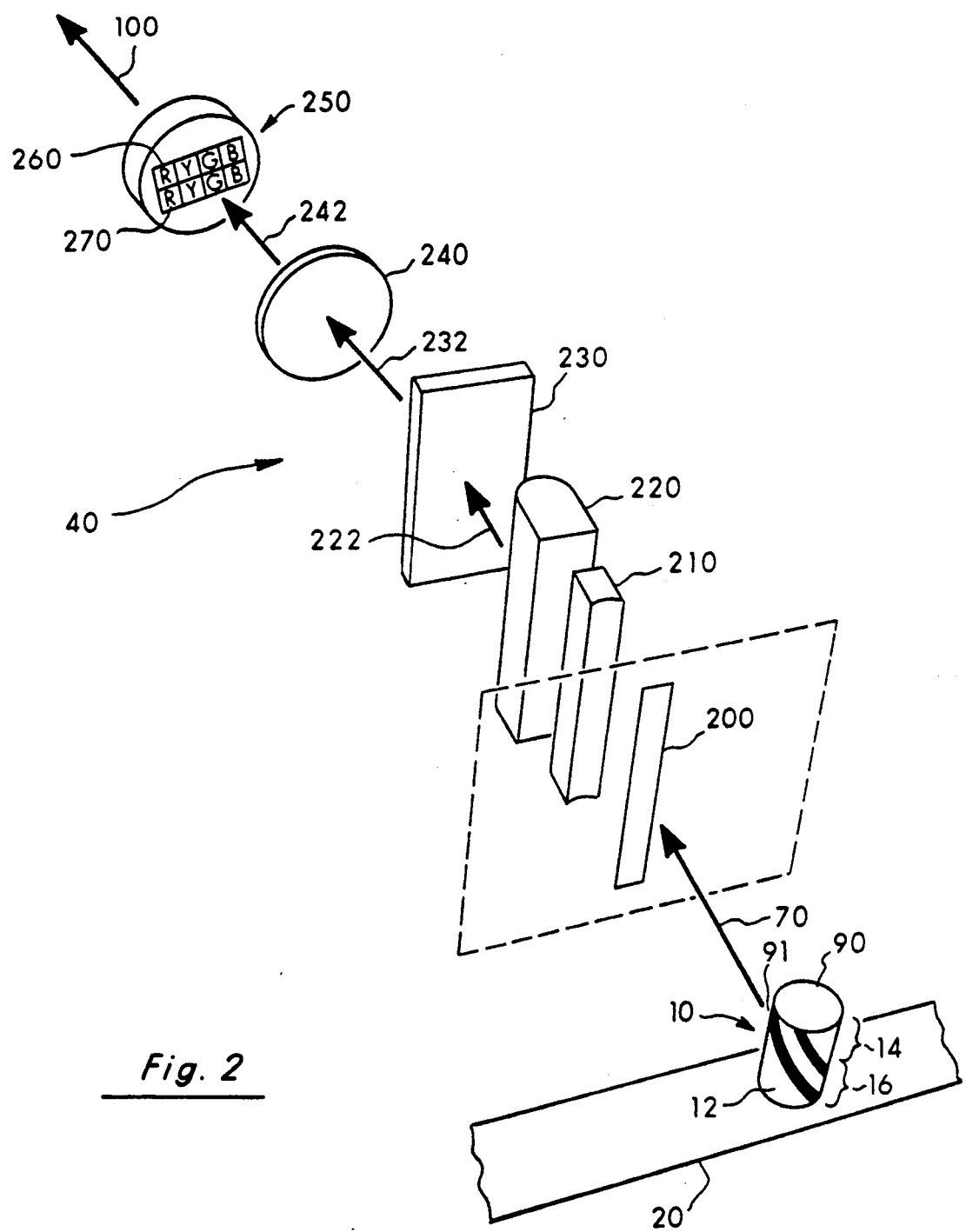
FIG. 2 is an exploded perspective view of the optical components in the optical head of the present invention.
Figure 3:
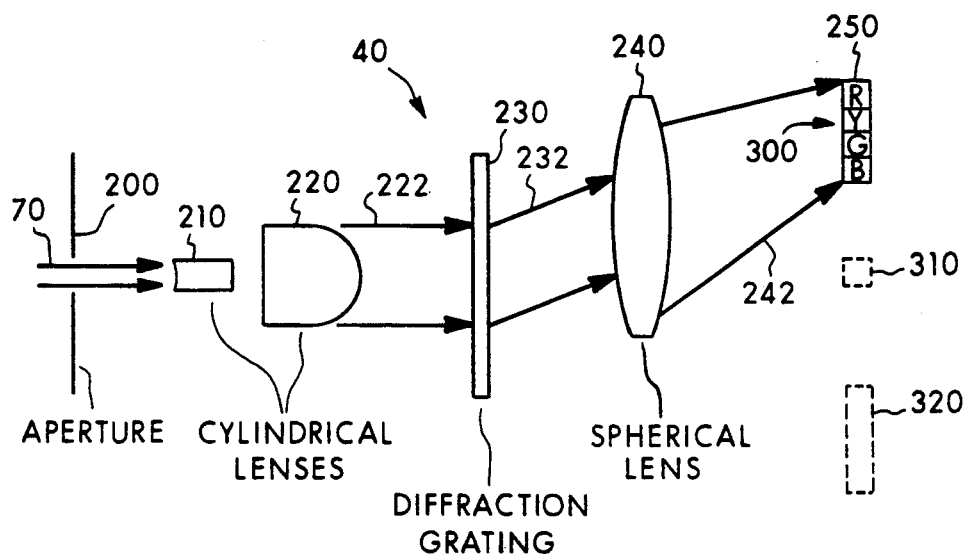
FIG. 3 is a side view of the optical components of FIG. 2 illustrating the placement of the detector array focal point in the positive first order image of the label.

In FIGS. 2 and 3, the optical components of the optical head 40 of the present invention are shown. The optical head 40 includes an aperture 200, cylindrical lenses 210 and 220, a diffraction grating 230, a spherical lens 240 and a detector array 250. Light 70 from the can 10 enters the optical head 40 through a limiting aperture 200 and passes through the cylindrical lenses 210 and 220. The light 222 leaving the last cylindrical lens 220 is collimated. In the preferred embodiment, the two cylindrical lenses 210 and 220 have focal lengths of −6.35 mm and +19 mm. The collimated light 222 then impinges on a diffraction grating 230 which separates the light 222 into its spectral components 232. In the preferred embodiment, the diffraction grating 230 is a ruled transmissive grating (600 lines per mm, 25 mm square). Any other diffractive element or a prism could be utilized. The separated light 232 is then delivered through a spherical lens 240 which focuses the light onto the array of photodiodes 250. The focused light is designated as 242 in FIG. 2. In the preferred embodiment, the spherical lens is 25 mm in diameter with a 30 mm focal length.

The photodiodes 250 comprise two rows 260 and 270 with each row containing four photodiodes. In the preferred embodiment, the photodiodes are preferably from Advanced Optoelectronics as Model No. 7000POH08M. This embodiment contains eight photodiodes in a single package, each photodiode having an integral preamplifier. The bottom row of diodes 270 detects light generated from the top 14 of can 10 whereas the top row of photodiodes 260 detects light reflected from the bottom 16 of can 10. Each diode in each of the rows views approximately one-fourth of the visible spectrum of the diffracted light.

Hence, as shown in FIG. 2, row 260 detects red R, yellow Y, green G, and blue B from left to right. The set of analog electrical signals from each photodiode are delivered over channels 100. Hence, the optical head 40 of the present invention as shown in FIGS. 2 and 3 outputs four analog color signals for the upper half 14 of the can 10 and four analog color signals for the lower half 16 of the can 10. As previously mentioned with respect to FIG. 1, this corresponds nominally to 180 degrees scan of one side 90 of can 10. With respect to the embodiment of FIG. 5, the three separate photo head assemblies 40a, 40b, and 40c would output eight analog color signals per head for a total of 24 signals.

In FIG. 3, the top view of the optical components of the optical head 40 of FIG. 2 is shown. This is important in that it shows that the first order image 232 from the diffraction grating is focused on the detector array 250. The top 14 of the can 10 being focused on the lower row 270 and the bottom 16 of the can 10 being focused on the upper row 260. As shown in FIG. 3, detector 250 is located in the focal area 300 in the first order image 232. The zero order image from the spherical lens 240 is located at 310 and the minus first order image is located at 320. The detector could also be placed at focal area 320. It is to be expressly understood that a prism could also be used for color separation (in which case only one image would result).

In summary, for each can 10 that passes by the optical head 40, a specific spatial area 91 of the can is viewed and a set of eight analog electrical signals are generated. Four channels (red, yellow, green, and blue) for the top 14 of can 10 and four channels (red, yellow, green, and blue) for the bottom 16 of can 10 on the side 90 facing the optical head. Each analog electrical signal corresponds to the color content located in the upper 14 or lower 16 portions of side 90 of can 10.

The reflected light received is generated by the light source 50. The light 60 contains wide spectral content across all colors of interest. The details on the can label modify the intensities of the various wavelengths of light 70 which reflect off the can label and into the sensor head 40. The amount that an individual label detail is able to alter the color signals from their nominal levels is dependent on the label details, field of view, etc. For example, if the top half of the can 90 were painted entirely red and the bottom half entirely blue, the relative analog magnitude of the output signals would be as follows:

$R_T$ = Large
$Y_T$ = Small
$G_T$ = Small
$B_T$ = Small
$R_B$ = Small
$Y_B$ = Small
$G_B$ = Small
$B_B$ = Large The above is an extreme example but one that illustrates the teachings of the present invention.

It is to be expressly understood that the present invention could operate without splitting the can 10 into top and bottom halves. In other words, the R, Y, G, and B signals could be generated by simply sensing these colors from the entire spatial area of the label in the field of view 70.

As mentioned, between can samples a dark sample is obtained which provides reference levels for the two sets of four output color signals. The use of this dark sample will be explained in greater detail later.

It is to be expressly understood that the optical head shown in FIGS. 2 and 3 comprise any set of suitable optics that could operate in a similar fashion to accomplish the teachings of the present invention. For example, a beam splitter could be used to split the reflected light into four separate optical paths with each optical path having a separate color filter disposed therein. Furthermore, the colors detected are not limited to four or to red, green, yellow, and blue. Any suitable number of colors or any suitable color choice could be utilized.

3. Electronic Components—

Figure 4:
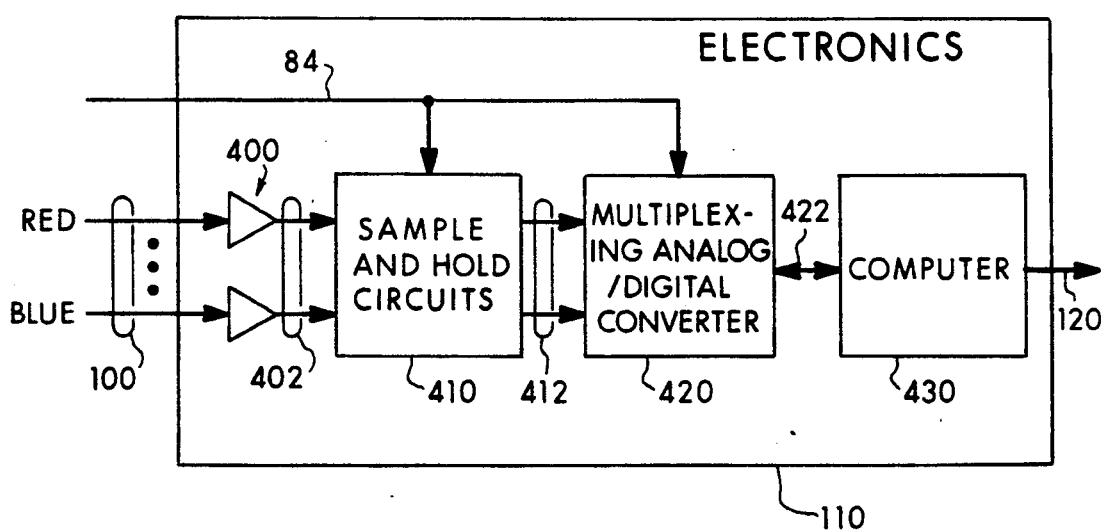
FIG. 4 sets forth the electronic block diagram components of the electronics of the present invention.

In FIG. 4, the electronic components 110 of the present invention are set forth. The signal sets are delivered over channels 100 from the detector 250 into amplifiers 400. The amplifiers are interconnected over lines 402 to sample and hold circuits 410 which in turn are connected over lines 412 to the multiplexing analog/digital converter 420. The converter 420 and sample and hold 410 receives the can position signals over lines 84 from the can sensor 80. The digital data sets are then transmitted over bus 422 into a computer 430 which generates the appropriate reject (error) signals, if any, over line 120.

The electrical color signals on lines 100 are amplified. This amplification occurs with amplifiers 400 which are typically located in the optical head 40. They are then delivered over a cable into a remote sample and hold circuit 410. In the preferred embodiment, a four-stage amplification circuit is used. The first stage of amplification is an integral part of the sensor 250. The second stage provides a signal gain about 90 v/v, the third stage provides nominal gain of about 12 v/v with adjustable offset and gain, and the fourth stage provides a gain of 1 v/v. Any suitable amplification design could be utilized.

The sample and hold circuits are triggered by the can position signal appearing on line 84 so each time the can position signal is generated, electrical signals 100 from the detector array 250 are sampled and stored. Hence, eight electrical color signals are sampled (one from each channel) for each can scanned. Samples are also taken between cans and this is termed a "dark" sample. Dark samples are used to remove system drift due to temperature changes, etc.

The can position sensor 80 generates a signal on line 84 which causes the sample and hold circuits 410 and analog to digital converter 420 to gather data from the eight color signals on channel 100. The can position sensor 80 is positioned so that when a can first breaks the light beam 82, neither it or the preceding can are in the field of view 70 of the sensor head 40. When the beam 82 is broken, the signal on line 84 causes the sample and hold 410 and converter 420 to collect the color signal data. Since only the black background 130 is viewed by the sensor, these data constitute what is termed a dark sample. When the can leaves the beam 82, it is in the center of the sensor head field of view 70. Again, the signal on line 84 causes the color signals on channel 100 to be sampled. These data are used to determine the can label characteristics. Hence, dark samples are collected between cans. It is to be understood that other timing arrangements could be provided and that the present invention is not to be limited to this approach.

The multiplexing analog/digital converter 420 converts the analog electrical color signal values into corresponding binary digitized values which are then delivered over lines 422 to computer 430. The multiplexing analog/digital converter and sample and hold circuit are activated by the can position signal on line 84. In the preferred embodiment the sample and hold 410 and the converter 420 are part of a single product from Analog Devices as Part No. RTI860. The converter 420 quantizes the analog signals to twelve bits with a resolution of 4.88 millivolts. Hence, for each set of eight samples (i.e., can samples or dark samples), 96 data bits are generated.

The computer receives the digitized data on bus 422 and, when appropriate, generates a can reject signal on line 120 or other suitable output inspection information over input/output 115. In the preferred embodiment the computer 430 is an 80286 based personal computer with 640 kilobytes of memory.

It is to be expressly understood that the electronic components 110 as shown in FIG. 4 could be of any suitable design which functions and performs in the manner described. The teachings of the present invention are not to be limited by the specific design shown in FIG. 4.

4. Operation—

Figure 6:
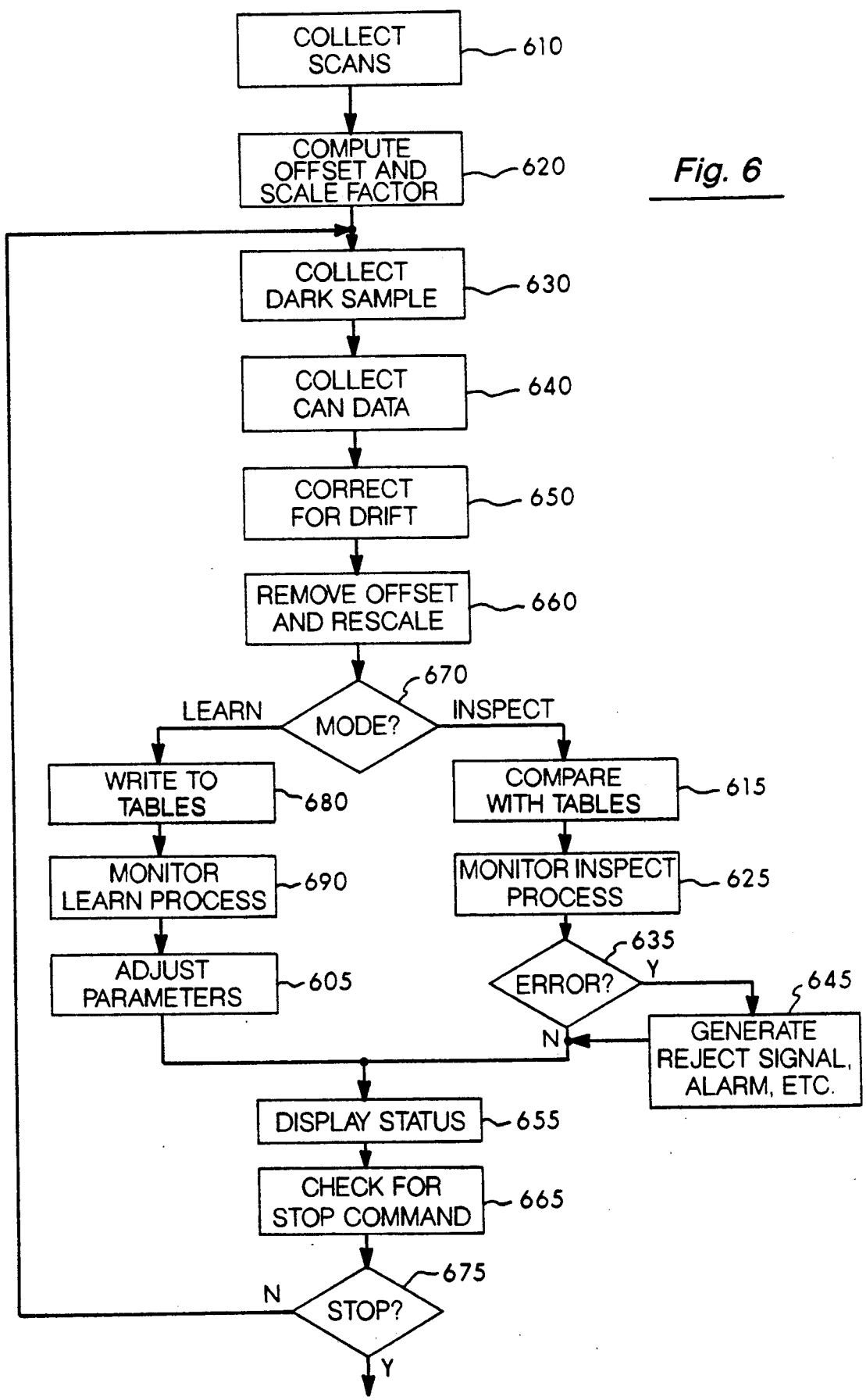
FIG. 6 sets forth the process flow utilized by the computer of the present invention to first learn and then automatically inspect labels.

In FIG. 6, the software flow diagram of the present invention is shown. Two modes of operation are disclosed. In the first mode, the present invention learns the label's color signature and constructs it and, in the second mode, the present invention inspects individual can labels.

Prior to entering stage 610, the software initializes the system by setting processing variables and operational parameters to default values. In the present invention, an operator menu is displayed which allows the operator to manually set operational parameters. After initialization, the system enters stage 610. In stage 610, the computer 430 directs the converter 420 to collect a number of can samples in succession. When the desired number of samples (approximately 100) have been collected, the computer enters stage 620 and reviews the data to determine the D.C. offset in each of the eight channels and the magnitude of the signal variation on each channel. Once determined, this information is stored in computer memory for use in later operations. Once stage 620 is complete, the computer begins the actual learn/compare process wherein stages 630 through 675 are executed once for each pass of a can.

In stage 630, a dark sample is collected. In this stage, the computer 430 directs the converter 420 to obtain a data sample from the sample and hold circuit 410 when the beam 82 in position sensor 80 is first broken by the leading edge of a can 10. When this beam is broken, the field of view 70 is positioned between the cans and, therefore, a dark sample is taken. Computer 430 stores these values in memory.

In stage 640, the computer 430 directs the converter 420 to transfer data sampled when the beam 82 is again sensed (i.e., the lagging edge of the can 10 passes allowing the beam to be again transmitted). Hence, the can 10 is directly in the field of view of the optical head. At this time, the computer stores in memory the values from channels 100 corresponding to the color signature portion of that can. It is to be understood that as mentioned the distances between the cans may vary. However, there is a minimum distance between the cans that must exist for the system of the present invention to obtain "dark samples."

Stage 650 is then entered and the system corrects for drift. For each channel, the dark sample value is subtracted from the can sample value. This removes the effects of drift in the amplifiers, long term variations of lamp intensity, and other variable factors which could effect the validity of the color reading. This occurs for each can and, therefore, results in highly stable data. The use of dark samples provides greater resolution in the analysis of the data generated by the present invention. However, the teachings of the present invention may be utilized without provision of such dark samples.

Stage 660 is then entered. The offsets in each channel as determined in stage 620 are removed and a scaling is applied to each channel as determined by the signal dynamics calculated in stage 620. These operations serve to accentuate the signal variations caused by the label characteristics. The offset removal and scaling functions are fixed throughout the learn/inspect modes of operation.

Stage 670 is then entered and a decision is made as to which operating mode should be entered. This is an automatic determination made by the computer 430 or there could be a manual override selected by the user of the present invention. In normal operation, however, computer 430 makes this decision.

A. Learning Mode of Operation

In stage 680, the values from the eight channels 100 are taken two at a time and are used to address locations in memory. In this manner, two-dimensional lookup tables are created. One table exists in memory for each combination of two data channels.

Two-dimensional mappings of the data occur from mapping one of the eight data channels 100 against data from a different channel. With eight data channels, a total number of 28 look-up tables can be constructed. Hence, under the teachings of the present invention, the actual number of data tables subsequently checked in inspection can be up to 28. A large number of data tables selected increases the sensitivity of the inspection process with the full 28 tables rendering the greatest sensitivity. The total number of 28 tables that can be constructed are set forth below:

| TABLE NUMBER | COLOR COMBINATION |
|---|---|
| 1 | $R_T R_B$ |
| 2 | $R_T Y_B$ |
| 3 | $R_T Y_T$ |
| 4 | $R_T G_B$ |
| 5 | $R_T G_T$ |
| 6 | $R_T B_T$ |
| 7 | $R_T B_B$ |
| 8 | $R_B Y_B$ |
| 9 | $R_B Y_T$ |
| 10 | $R_B G_B$ |
| 11 | $R_B G_T$ |
| 12 | $R_B B_B$ |
| 13 | $R_B B_T$ |
| 14 | $Y_T Y_B$ |
| 15 | $Y_T G_B$ |
| 16 | $Y_T G_T$ |
| 17 | $Y_T B_B$ |
| 18 | $Y_T B_T$ |
| 19 | $Y_B G_B$ |
| 20 | $Y_B G_T$ |
| 21 | $Y_B B_B$ |
| 22 | $Y_B B_T$ |
| 23 | $G_B G_T$ |
| 24 | $G_B B_B$ |
| 25 | $G_B B_T$ |
| 26 | $G_T B_B$ |
| 27 | $G_T B_T$ |
| 28 | $B_B B_T$ |

Where:
R = Red, B = Blue, G = Green, Y = YELLOW
Subscript B = Bottom
Subscript T = Top It is to be understood that more or less than four colors could be selected, thereby creating different total numbers of tables. For example, five colors for each half of the can (i.e., 10 channels) would generate 45 look-up tables.

While the preferred embodiment uses two dimensional tables, it is to be understood that any multi-dimensional table could be utilized. Also, while the present invention separately provides different color analog signals for upper and lower portions of can 10, it is to be understood that the optical head could analyze more than or less than two portions through a redesign of the optical components. Each resultant address to a two-color individual table points to a single bit in memory. This is illustrated in FIG. 7.

Figure 7A:
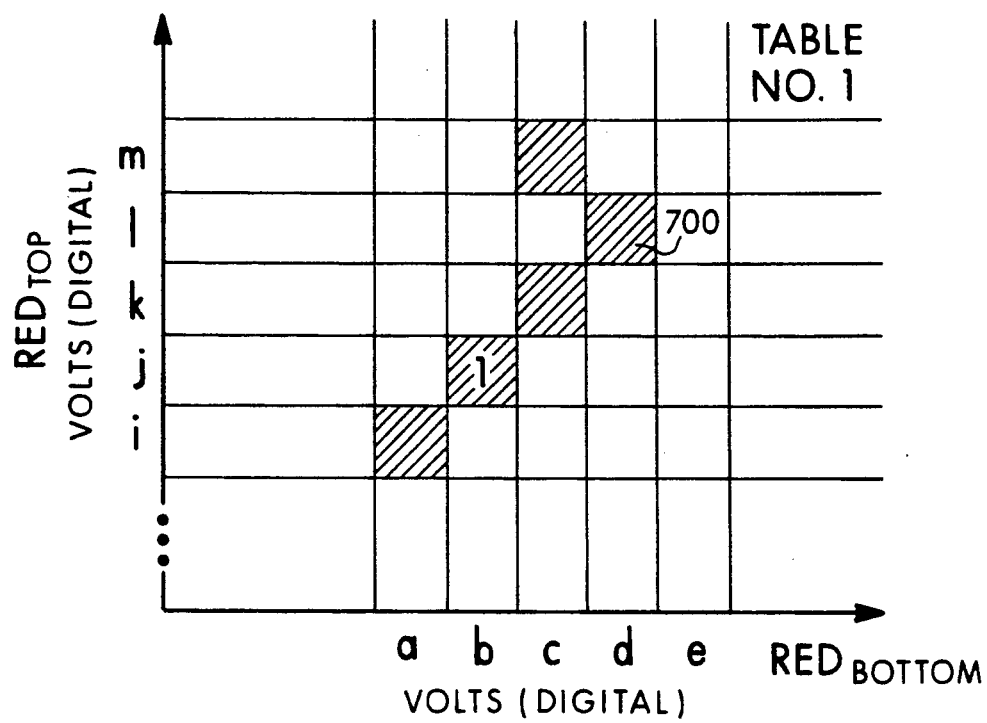
FIGS. 7a and 7b are graphical illustrations of the look-up tables of the present invention.

In FIG. 7(a), Table 1 corresponding to the color combination $R_T R_B$ is set forth. Assume in stage 680 that an individual scan of the spatial area 91 of can 10 has occurred. The resulting $R_T$ and $R_B$ values are used to map to Table 1 at locations j and b, where j equals the digital value in volts of the red color from the top of the can and b equals the digital value in volts of the red color from the bottom of the can. As shown in FIG. 7(a), a value of one is placed in Table 1. This forms a part of the overall color signature which is shown by the shaded gray boxes 700.

Figure 7B:
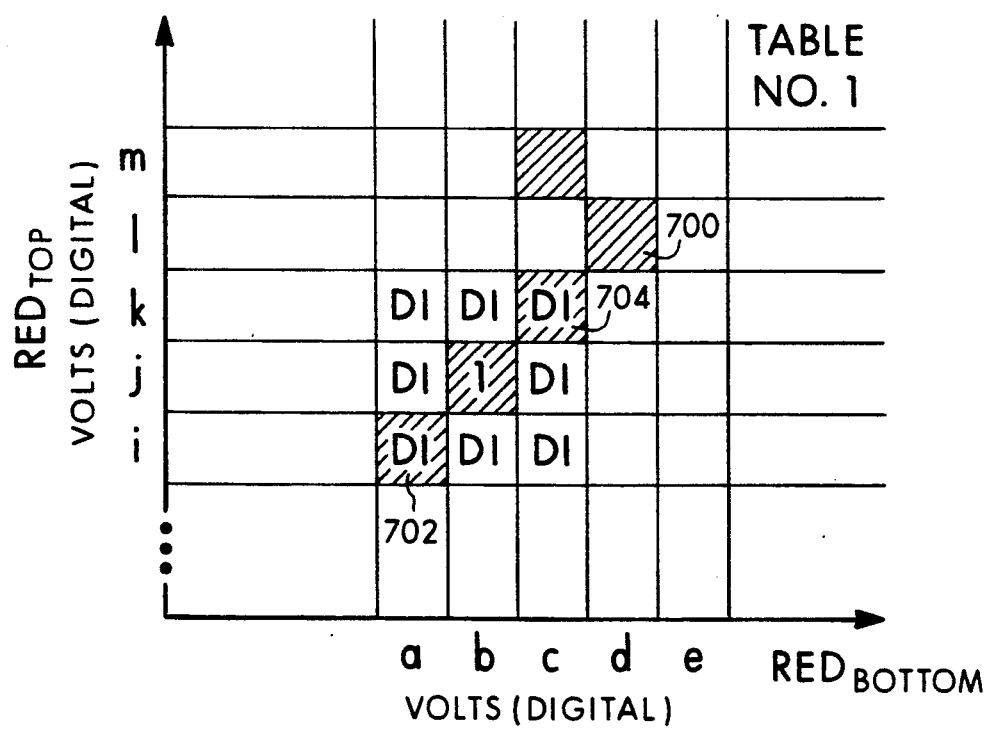

In the learn mode, location j, b is addressed and the bit in memory is set to a logical one. Depending upon the amount of dilation (as specified by one of the operational parameters), a number of additional bits surrounding the central bit are also set to one. Dilation of "one" causes the 8 neighboring contiguous bits to be set. Dilation of "two" causes the 24 neighboring contiguous bits to be set to one. Dilation is used as a processing technique to fill in missing parts of the color signature curve 700 thereby shortening the learning cycle which will be discussed in greater detail in the illustration. In FIG. 7(b), the "one" entered in FIG. 7(a) is shown with a dilation of one, D1. With a dilation of one, the eight neighboring contiguous bits around the j, b bit are automatically set to "one" in stage 680.

As can be seen in FIG. 7(b), two positions adjacent to the aforementioned entry at j,b also lie on the signature curve 700. These two adjacent entries are labeled 702 and 704. Clearly, if no dilation were utilized in writing the central bit at j,b, additional scans would have to be collected by the system to eventually also include bits 702 and 704. If dilation is used when writing to the tables, adjacent bits also are set thus significantly reducing the number of scans required to build a set of signature tables. The effect of dilation on subsequent inspection operations may also be observed from the example of FIG. 7(b). In addition to connecting adjacent bits, dilation broadens the resultant signature curve.

In an inspection of a label if the resultant data point was close to the nominal signature curve 700, and if no dilation were applied to the mapping data when it was written, the inspection would fail the label. If the mapping data were dilated, then the inspection might pass the object. Thus, sensitivity of the present invention can also be adjusted with the level of dilation. Stage 690 is now entered.

After the results of each scan are written to the tables, the process of color signature construction is monitored in stage 690. The purpose of this stage is to evaluate the progress of learning. Stage 605 is now entered. In this stage, and based upon the results of stage 690, the operational parameters are adjusted. If the number of past scans causing no new table entries is equal to a predetermined threshold, then the learn process is deemed to be complete and the mode 670 is switched to the inspect mode. Again, this will be discussed and illustrated subsequently. Suffice to say, if a series of data sets are obtained in the learn mode which do not add any new information to the tables being constructed, (i.e., a threshold has been reached), then in fact the color signature for the label is fully constructed.

Finally, because of the split into the top and bottom sets of signals from the field of view, the presence of the same color can be compared from each set: $R_T R_B$, $G_T G_B$, $Y_T Y_B$, $B_T B_B$ in creating a unique color signature. Also, the top colors can be compared to the bottom colors to create a unique color signature: $R_T G_B$, $R_T B_B$, $R_T Y_B$, etc. This novel approach increases sensitivity to defects—i.e. essentially comparing a color signal from one area on the label to a color signal from another area on the label.

B. Inspection Mode of Operation

After construction of the color signature has occurred, stage 615 is entered. Each new can which is scanned results in analog color output values on channels 100 which then are converted to digital color value and compared with the color signatures stored in the tables. Hence, the values from the eight channels 100 are again taken two at a time and used to address the locations in the associated tables. The computer checks all tables in this manner and determines what bits are set (indicating that a particular combination of data values has been previously learned).

Stage 625 is then entered. The results of the table comparisons are used to evaluate whether or not that particular can being scanned passes or fails. Predetermined operational parameters specify whether the can data which is sampled must compare positively with all of the tables, a certain number of tables, or a specific subset of tables in order to pass. Again, one of the characteristics of the present invention is the ability to modify the sensitivity of defect detection. Hence, in stage 635, if an error is found, stage 645 is entered and a reject signal, alarm, or other suitable indication of error is issued. Stage 625 is also capable of generating necessary pass/fail statistics which can be computed for a predetermined number of previous consecutive scans. This is another metric which may be used in decision block 635 to determine whether or not a process error condition exists.

Stage 655 is then entered. A video display terminal is optionally provided so that learn or inspect performance data may be viewed by the operator.

Finally, stage 665 is entered. The operator has the optional right to use an input device 115 so that the operator may stop the system. If not, in stage 675 the system continues.

C. Actual Can Data

FIG. 8 sets forth four plots showing part of the data for a DR. PEPPER ® can signature. This can was placed in the sensor field of view 70 and simply rotated 720° while data samples were collected in order to create the color signatures. FIG. 8(a) shows the analog output for two data channels. The top trace 800 corresponds to the red color value from the bottom 16 of the can which is termed $R_B$. The bottom trace 810 is the color signal for the channel corresponding to the red color signal for the upper 14 half of the can 10 which is termed $R_T$. FIG. 8(b) is the same data from FIG. 8(a) after the offset is removed in stage 660 and after rescaling. In FIG. 8(a), the horizontal axis represents 3000 samples and the vertical axis scales from 0 to 10 volts. In FIG. 8(b), the vertical scale now represents a total deviation of 0.833 volts for the 3000 samples clearly emphasizing the color variations.

Figure 8B:
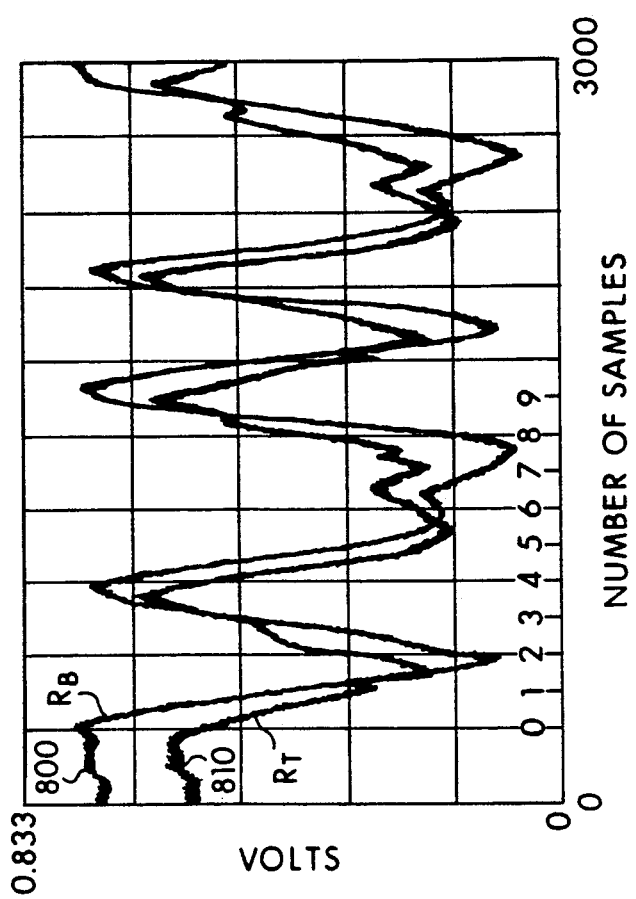
FIGS. 8a–8d set forth a variety of actual data curves obtained by the present invention.
Figure 8A:
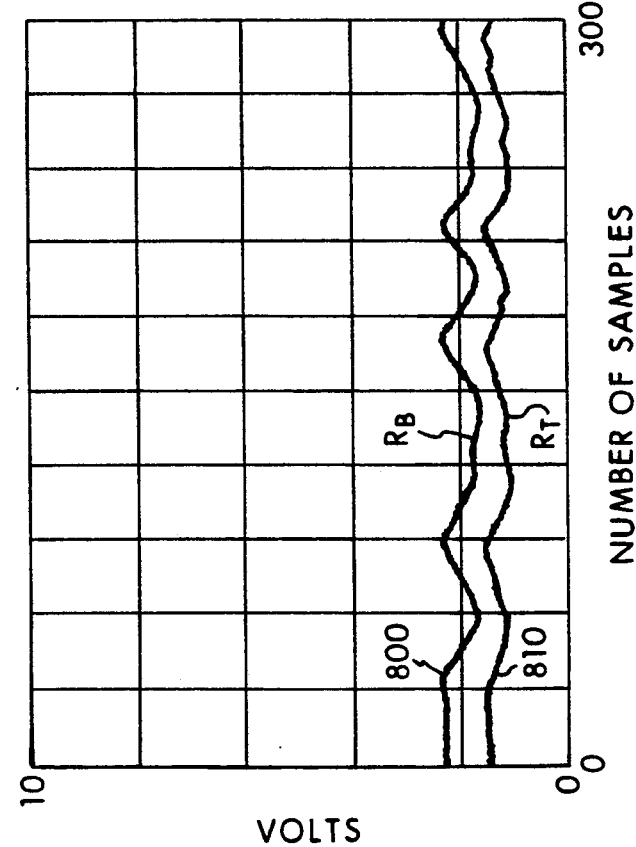
Figure 8C:
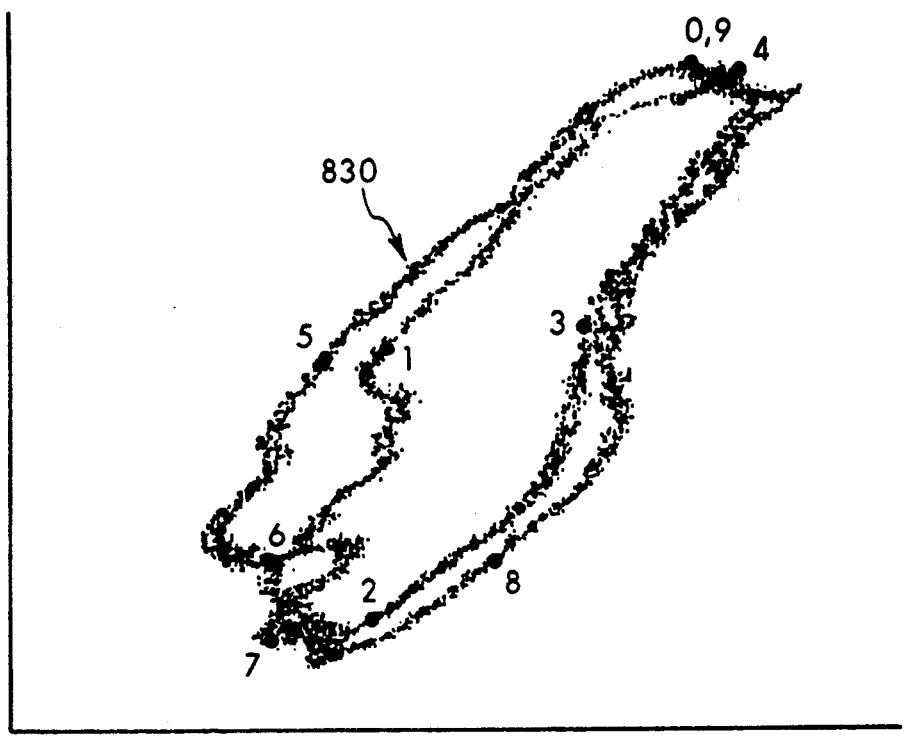

FIG. 8(c) sets forth the two dimensional memory table for $R_T R_B$ with no dilation. A large proportion of the color signature curve 830 has open space between the adjacent data points and if this table were used in inspection of the cans, a large share of good cans would necessarily fail. It is clear, upon inspection of FIG. 8(c), that under this condition 3000 samples are insufficient for the learning process and, therefore, the signature 830 of FIG. 8(c) is not fully constructed. In fact, for the learning curve 830 to be fully constructed would require many tens of thousands more can samples for it to be complete.

Figure 8D:
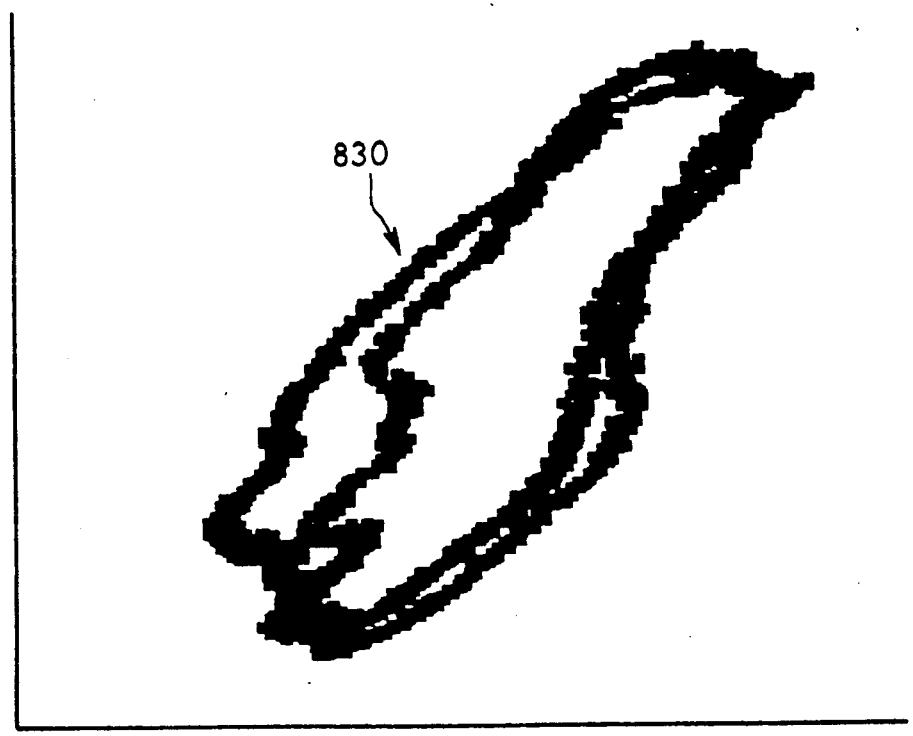

In FIG. 8(d), a dilation of 5 is utilized when writing to the data table. For a dilation of 5, 80 neighboring contiguous bits are set for each measured point. As can be witnessed, there are no gaps in FIG. 8(d) and the use of a dilation equal to five allows the learning process for this example of a DR. PEPPER ® can to be completed after 3000 samples. Clearly, dilation can be used to speed the learning process.

At this point, it is useful to discuss points labelled 0 through 9 of FIGS. 8(b) and 8(c). In FIG. 8(b), points 0 through 9 indicate a set of points representing a single 360 degree rotation of the DR. PEPPER ® can. These represent discrete points of rotation (i.e., at 360 degrees around the can). These points are then indicated in FIG. 8(c) as discrete points on the color signature curve 830. These are just subsets of the overall 3000 points collected. As the can is rotated, in this example, (or as each can passes the optical head 40 in the production line) new data is added to the signature curve 830. The new data can be simply a single bit or multiple bits in the case when dilation is utilized. When no new data combinations have been detected (i.e., in a production line such as 2000 cans passing the optical head), then the learn process is complete.

In addition to dilation, certain other morphologic operations such as erosion, point/edge linking can be utilized to speed the learning process. In addition to speeding the learning process, such operations can be used to vary the sensitivity of the subsequent inspection operations by artificially broadening or thinning the learned data.

In conclusion, FIG. 6 is a block diagram of the data processing functions performed by the computer 430. The eight channels 100 of digitized signals are gathered for each can by the optical head. As shown in FIG. 6, the process is automatic with the system first learning the color signatures of a can label and once satisfied with the learning process, automatically switching over to commence inspecting. Normally, the operator initiates only the learned process with all of the functions being automatic. It is to be expressly understood, however, that variations on that process could occur wherein the operator could manually cause the system to learn the color signatures for a label and then manually cause the system to commence inspection.

Furthermore, the method employed by the computer 430 of storing the learned data has the advantage of allowing for an unlimited number of learned data points to be taken and stored. Each table need only be large enough to accommodate the desired range of data values from each channel. Thus, all learned data will be mapped into each table regardless of the amount of data collected. Additionally, the simplicity of the data processing for the learn and inspection processes allows for the operation of learning and inspection to occur at very high can transfer rates such as 2,000 cans per minute.

It can be observed from the above that the system of the present invention can be used either as a process monitor inspecting a series of cans or as a single-can inspection tool. When the present invention is used as a process monitor, the sensitivity of the system is adjusted to a maximum and the fault threshold is such that an alarm indicator is generated if a drift in the label signatures is detected over a number of can passes.

In the single-can inspection application, the system of the present invention has its fault sensitivity adjusted to generate a reject indicator for single labels having color signatures significantly different from the learned signature. In such an application, the computer can generate the necessary signals to drive a can reject mechanism, not shown, to remove the can from the assembly line.

The present invention can be used to inspect items with non-varying signatures just as well as those with varying signatures. Learning in this case would be extremely fast, requiring only a few scans. Inspection of continuous sheets of material such as coated metal is an example. The can position sensor would be replaced by a clock pulse train, or by the output of a shaft encoder, thus commanding the present invention to perform an inspection periodically or every few inches.

The inspection resolution of the sensor of the present invention is dependent on the detail of the object being inspected, the dimensions of the field of view, the number of cans utilized in the learn process, and the amount of dilation performed when writing into the tables. While it can be easily stated that the present invention will detect defects that fill the instantaneous field of view of one of the detector elements, stating the minimum detectable defect dimensions is nearly impossible. In laboratory experiments in which the present invention viewed nearly 180 degrees of the can circumference every pass, small label defects created by placing 1 cm-square pieces of tape on the can were detected a high percentage of the time. It can be expected that smaller defects of similar design would be detected if smaller individual fields of view were utilized.

It is to be expressly understood that the claimed invention is not to be limited to the description of the preferred embodiment but encompasses other modifications and alterations within the scope and spirit of the inventive concept.

We claim:

1. An optical inspection system for inspecting for the presence of defects in identical colored labels, said optical inspection system comprising:

means (20) for conveying said labels, said labels being randomly oriented on said conveying means, means (40, 50, 80) positioned near said labels as said randomly oriented labels are conveyed by said conveying means for sensing in each of said labels, independent of the speed of said conveying means, the presence of a selected number of colors (R, B, Y, G) appearing in a predetermined field of view (70) of a spatial area of each said label, said sensing means producing a set of analog electrical signals for each of said selected number of colors sensed in said predetermined field of view from said spatial area of each said label, means (110) connected to said sensing means for processing each set of said analog electrical signals, said processing means further comprises:

(a) means for generating (680, 690, 605) a multi-dimensional color signature (830) for the entire area of said label based upon said selected number of colors, said multi-dimensional color signature being fully generated when a sufficient number of said randomly oriented labels have passed said sensing means so that said entire area of said label has been sensed, (b) means for comparing (615, 625, 635) the analog electrical signal to said generated multi-dimensional color signature, said processing means issuing a fail signal when a desired multi-color combination of said analog electrical signals does not match said multi-dimensional color signature.

2. The optical inspection system of claim 1 wherein said processing means further comprises:

means (410) connected to said sensing means for holding each said set of analog electrical signals from said sensing means, means (20) connected to said holding means (410) for converting each said set of held analog electrical signals into a set of corresponding digital signals for each of said selected number of colors.

3. The optical inspection system of claim 1 wherein said sensing means further comprises:

an aperture (200) for limiting light from said spatial area in said predetermined field of view, a pair of cylindrical lenses (210, 220) receiving said limited light from said aperture for collimating said limited light, a diffraction grating (230) receiving said collimated light from said pair of cylindrical lenses for diffracting said collimated light, a spherical lens (240) receiving a first order image of said diffracted light for focusing said first order image, and a detector array (250) in the focal area of said first order image.

4. The optical inspection system of claim 1 wherein said sensing means further comprises:

means (50) for generating light onto said randomly oriented labels, a sensor (40) for receiving reflected light from each of said randomly oriented labels, said reflected light comprising light from said generating means, means (130) located opposite said sensing means and behind each of said randomly oriented labels for providing a uniform dark background.

5. The optical inspection of claim 4 further comprising:

means (80) for detecting the presence of each label for issuing control signals, said sensing means connected to said detecting means and receptive of said control signals for producing a first set of analog electrical signals for each of said selected number of colors when each of said randomly oriented labels are conveyed by said conveying means into said predetermined field of view and a second set of analog electrical signals for each of said selected number of colors when the space between each of said randomly oriented labels are in said predetermined field of view so as to provide a reference set of analog electrical signals corresponding to said uniform dark background.

6. The optical inspection system of claim 1 wherein said set of analog electrical signals comprises a first subset of color signals from first sub-area of said spatial area and a second subset of color signals from a second sub-area of said spatial area.

7. The optical inspection system of claim 6 wherein said first subset of colors comprises: green, yellow, blue and red and wherein said second subset of colors comprises: green, yellow, blue and red.

8. The optical inspection system of claim 6 wherein said generating means provides separate two dimensional color signatures between said first and second subset of color signatures.

9. The optical inspection system of claim 1 wherein said generating means further provides dilation to said generated color signature so as to speed up said generation.

10. An optical inspection system for inspecting for the presence of defects in a colored label (12) placed on the sidewalls of cylindrical containers (10), said optical inspection system comprising:
   means (20) for conveying said containers in a production line (120), said containers being randomly oriented,
   means (40) positioned near said containers as said containers move along in said production line for sensing in said colored label on each of said containers the presence of a selected number of colors (R, B, Y, G) appearing in the predetermined field of view (70), said sensing means producing an analog color signal for each of said selected number of colors,
   means (110) connected to said sensing means for processing each said analog electrical signal, said processing means further:
   (a) generating (680, 690, 605) a plurality of two color signatures (830) based upon said selected number of colors, said two color signatures being fully generated when a sufficient number of said randomly oriented containers have passed said sensing means so that all spatial areas of said label have been sensed,
   (b) comparing (615, 625, 635) said analog electrical signals to said generated plurality of two color signatures, said processing means issuing an error signal (120) when a desired two-color combination of said analog electrical signals does not match the corresponding two color combination signature.

11. The optical inspection system of claim 10 wherein said processing means further comprises:
   means (410) connected to said sensing means for holding each said analog electrical signals from said sensing means,
   means for 20 connected to said holding means (410) for converting each said analog electrical signal into a corresponding digital signal for each of said selected number of colors.

12. The optical inspection system of claim 10 wherein said sensing means further comprises:
   an aperture (200) for limiting light from said predetermined field of view,
   a pair of cylindrical lenses (210, 220) receiving said limited light from said aperture for collimating said limited light,
   a diffraction grating (230) receiving said collimated light from said pair of cylindrical lenses for diffracting said collimated light,
   a spherical lens (240) receiving a first order image of said diffracted light for focusing said first order image, and
   a detector array (250) in the focal area of said first order image.

13. The optical inspection system of claim 10 wherein said sensing means further comprises:
   means (50) for generating light onto said randomly oriented labels,
   a sensor (40) for receiving reflected light from each of said randomly oriented labels, said reflected light comprising light from said generating means,
   means (130) located opposite said sensing means and behind each of said randomly oriented labels for providing a uniform dark background.

14. The optical inspection of claim 13 further comprising:
   means (80) for detecting the presence of each can for issuing control signals,
   said sensing means connected to said detecting means and receptive of said control signals for producing a first set of analog electrical signals for each of said selected number of colors when each of said randomly oriented labels are conveyed by said conveying means into said predetermined field of view and a second set of analog electrical signals for each of said selected number of colors when the space between each of said randomly oriented labels are in said predetermined field of view so as to provide a reference set of analog electrical signals corresponding to said uniform dark background.

15. The optical inspection system of claim 10 wherein said analog electrical signals comprises a first subset of color signals from first sub-area of said spatial area and a second subset of color signals from a second sub-area of said spatial area.

16. The optical inspection system of claim 15 wherein said first subset of colors comprises: green, yellow, blue and red and wherein said second subset of colors comprises: green, yellow, blue and red.

17. The optical inspection system of claim 15 wherein said generating means provides separate two dimensional color signatures between said first and second subset of color signatures.

18. The optical inspection system of claim 10 wherein said generating means further provides dilation to said generated color signature so as to speed up said generation.

19. An optical inspection system for inspecting for the presence of defects in colored label (12) placed on the sidewalls of cylindrical beverage cans (10), said optical inspection system comprising:
   means (20) for conveying said beverage cans along a linear path (120), said beverage cans being randomly oriented (30), having uneven spacing (D1, D2) between beverage cans, and being located unevenly about the center line (CL) of said linear path,
   means (40, 50, 80) positioned near said beverage cans as said beverage cans move along said linear path for sensing the presence of a selected number of colors (R, B, Y, G) appearing in a predetermined field of view (70), said sensing means producing a first signal (100) for each of said selected number of colors in said reflected light, said sensing means producing a second signal for each of said selected number of colors when said field of view is between successive beverage cans,
   means (110) connected to said sensing means for processing each said first and second sets of signals, said processing means further comprising:
   (a) means (80, 130) receptive of said first and second sets of signals for correcting said first set of signals for drift based upon said second set of signals,
   (b) means receptive of said first set of signals for generating (680, 690, 605) a plurality of two color signatures based upon said selected number of colors of corrected signals, said two color signatures (830) being fully generated when a sufficient number of said beverage cans have passed said sensing means so that all spatial areas of said label have been sensed, (c) comparing (615, 625, 635), said analog electrical signals to said generated plurality of two color signatures, said means issuing an error signal (120) when a desired two-color combination of said analog electrical signals fails to match the corresponding two color combination signature.

20. An optical inspection system for inspecting for the presence of defects in identical colored labels, said optical inspection system comprising:

means (20) for conveying said labels, said labels being randomly oriented on said conveying means, means (40, 50, 80) positioned near said labels as said randomly oriented labels are conveyed by said conveying means for sensing in each of said labels, independent of the speed of said conveying means, the presence of a selected number of colors (R, B, Y, G) appearing in a predetermined field of view (70) of a spatial area of each said label, said sensing means comprising at least:

(a) means (200) for limiting light from said spatial area in said predetermined field of view, (b) means (210, 220) receiving said limited light from said limiting means for collimating said limited light, (c) means (230) receiving said collimated light from said collimating means for diffracting said collimated light, (d) means (240) receiving a first order image of said diffracted light from said diffracting means for focusing said first order image, and (e) means (250) in the focal area of said first order image for producing a set of analog electrical signals for each of said selected number of colors sensed in said predetermined field of view from said spatial area of each said label, means (110) connected to said sensing means for processing each set of said analog electrical signals, said processing means further comprises:

(a) means for generating (680, 690, 605) a two-dimensional color signature (803) for the entire area of said label based upon said selected number of colors, said two-dimensional color signature being fully generated when a sufficient number of said randomly oriented labels have passed said sensing means so that said entire area of said label has been sensed, said generating means providing dilation while generating said color signature in order to speed up said generation, (b) means for comparing (615, 625, 635) the analog electrical signal to said generated two-dimensional color signature, said processing means issuing a fail signal when a desired two-color combination of said analog electrical signals does not match said two-dimensional color signature.

21. A method for optical inspection of defects in colored label (12) placed on the sidewalls of cylindrical beverage cans (10), said method comprising the steps of:

conveying (20) the beverage cans along a path (120), said beverage cans being randomly oriented (30), having uneven spacing (D1, D2) between beverage cans, and being located unevenly about the center line (CL) of said linear path, sensing in the reflected light from said colored label on each of said beverage cans the presence of a selected number of colors (R, B, Y, G) appearing in a predetermined field of view (70) as the cans move in the path, producing a first signal (100) for each of said selected number of colors in said reflected light, producing a second signal for each of said selected number of colors when said field of view is between successive beverage cans, correcting said first set of signals for drift based upon said second set of signals, generating a plurality of two color signatures based upon said selected number of colors of corrected signals, said two color signatures (830) being fully generated when a sufficient number of said beverage cans have passed said sensing means so that all spatial areas of said label have been sensed, comparing (615, 625, 635), said analog electrical signals to said generated plurality of two color signatures, issuing an error signal (120) when a desired two-color combination of said analog electrical signals fails to match the corresponding two color combination signature.

22. A method for optical inspection of defects in colored labels (12), said method comprising the steps of:

conveying (20) randomly oriented labels along a path (120), sensing, from the reflected light from said colored label, the presence of a selected number of colors (R, B, Y, G) appearing in a predetermined field of view (70) as the labels move in the path, producing a first set of signals for each of said selected number of colors in said reflected light from a first portion of said predetermined field of view, producing a second set of signals for each of said selected number of colors in said reflected light from a second portion of said predetermined field of view, generating a plurality of multi-color signatures based upon a said selected number of signals from said first and second sets, said multi-color signatures (830) being fully generated when a sufficient number of said labels have passed said sensing means so that all areas of said label have been sensed, comparing (615, 625, 635), the first and second sets of signals to said generated plurality of multi-color signatures, issuing an error signal (120) when a desired multi-color combination of said analog electrical signals fails to match the corresponding multi-color combination signature.

* * * * *

UNITED STATES PATENT AND TRADEMARK OFFICE
CERTIFICATE OF CORRECTION

PATENT NO. : 5,120,126

DATED : June 9, 1992

INVENTOR(S) : Ronald D. Wertz, Jeffrey P. Davies, Robert H. Cormack

It is certified that error appears in the above-identified patent and that said Letters Patent is hereby corrected as shown below:

Title Page:
In the abstract, line 26, delete "air signal" and substitute --error signal--

Signed and Sealed this

Twenty-eighth Day of September, 1993

Attest:

BRUCE LEHMAN

Attesting Officer

Commissioner of Patents and Trademarks